United States Patent
Maliglowka et al.

(10) Patent No.: US 8,057,502 B2
(45) Date of Patent: Nov. 15, 2011

(54) SURGICAL OBTURATOR

(75) Inventors: Johann Maliglowka, Kolbingen (DE); Rupert Mayenberger, Rielasingen (DE); Tom Schweitzer, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 353 days.

(21) Appl. No.: 12/313,660

(22) Filed: Nov. 21, 2008

(65) Prior Publication Data
US 2009/0138034 A1   May 28, 2009

Related U.S. Application Data

(63) Continuation of application No. PCT/EP2007/003881, filed on May 3, 2007.

(30) Foreign Application Priority Data

May 27, 2006  (DE) .......................... 10 2006 024 757

(51) Int. Cl.
*A61B 17/34* (2006.01)

(52) U.S. Cl. ........................................ 606/185; 606/172

(58) Field of Classification Search .......... 604/110–111, 604/158, 164.01, 164.08, 167.01, 192; 606/108, 606/184–185
See application file for complete search history.

(56) References Cited

U.S. PATENT DOCUMENTS

| | | | |
|---|---|---|---|
| 3,051,132 A | 8/1962 | Johmann | |
| 5,066,288 A | 11/1991 | Deniega et al. | |
| 5,215,526 A | 6/1993 | Deniega et al. | |
| 5,324,268 A | 6/1994 | Yoon | |
| 5,342,382 A * | 8/1994 | Brinkerhoff et al. | 606/184 |
| 5,346,459 A | 9/1994 | Allen | |
| 5,360,405 A | 11/1994 | Yoon | |
| 5,423,770 A | 6/1995 | Yoon | |
| 5,462,532 A | 10/1995 | Gresl | |
| 5,569,289 A | 10/1996 | Yoon | |
| 5,591,191 A | 1/1997 | Kieturakis | |
| 5,609,604 A * | 3/1997 | Schwemberger et al. | 606/185 |
| 5,645,076 A | 7/1997 | Yoon | |
| 5,662,673 A | 9/1997 | Kieturakis | |
| 5,674,237 A | 10/1997 | Ott | |
| 5,676,156 A * | 10/1997 | Yoon | 600/567 |
| 5,755,697 A | 5/1998 | Jones et al. | |
| 5,779,680 A | 7/1998 | Yoon | |
| 5,807,402 A | 9/1998 | Yoon | |

(Continued)

FOREIGN PATENT DOCUMENTS

DE    44 11 685    10/1995

(Continued)

*Primary Examiner* — Tom Hughes
*Assistant Examiner* — Rachel S Papeika
(74) *Attorney, Agent, or Firm* — Lipsitz & McAllister, LLC

(57) ABSTRACT

In a surgical obturator for piercing a body wall, comprising a tubular housing that at one end forms an introduction tip with a continuously decreasing diameter, and comprising a blade projecting from the introduction tip for making an incision in the body wall, in order to reduce the risk of injury during piercing of the body wall it is proposed that the introduction tip comprises a central protective cap, which is displaceable in longitudinal direction relative to the introduction tip between an advanced inoperative position and a retracted working position, that the blade in the housing is displaceable in longitudinal direction between an advanced cutting position and a retracted protected position, that disposed in the housing is a retraction device that displaces the blade from the cutting position into the protected position, and that the retraction device may be activated by a displacement of the protective cap from the working position into the inoperative position.

17 Claims, 8 Drawing Sheets

U.S. PATENT DOCUMENTS

2003/0100914 A1   5/2003   O'Heeron et al.

FOREIGN PATENT DOCUMENTS

| DE | 197 18 086 | 11/1998 |
| DE | 20 2006 008 405 | 7/2006 |
| DE | 20 2006 008 406 | 7/2006 |
| DE | 20 2006 018 883 | 2/2007 |
| EP | 0 135 364 | 3/1985 |
| EP | 0 495 633 | 7/1992 |
| EP | 0 499 457 | 8/1992 |
| EP | 0 551 968 | 7/1993 |
| EP | 0 600 921 | 6/1994 |
| EP | 0 705 077 | 4/1996 |
| WO | 89/03661 | 5/1989 |

\* cited by examiner

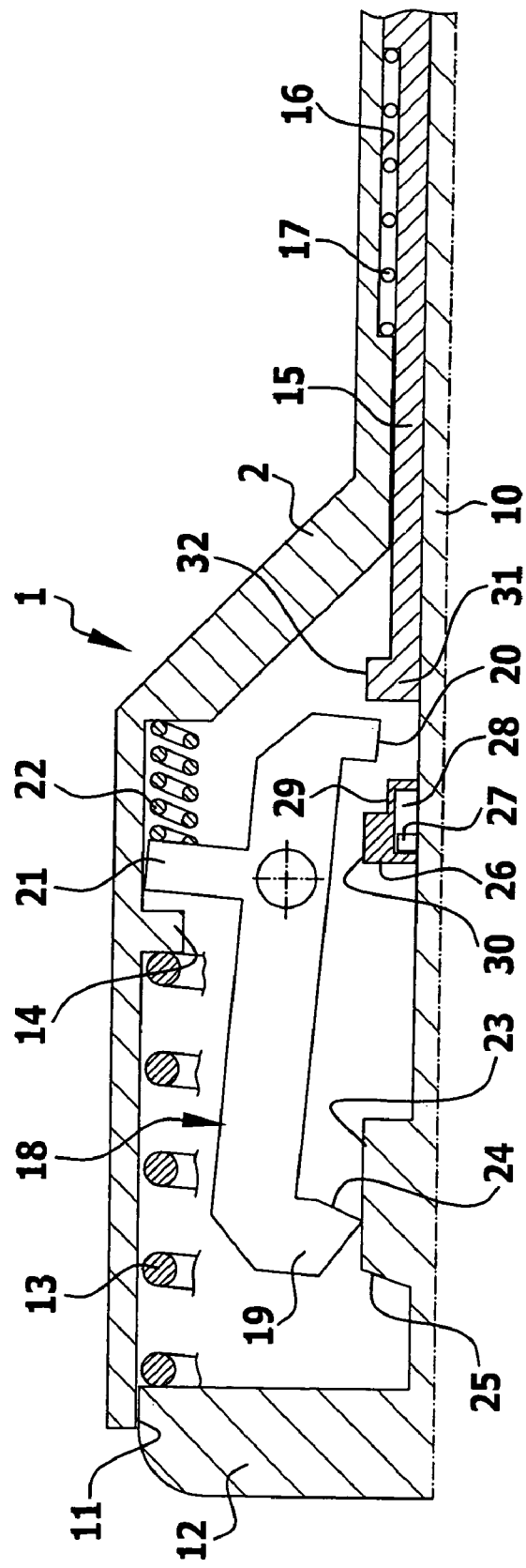

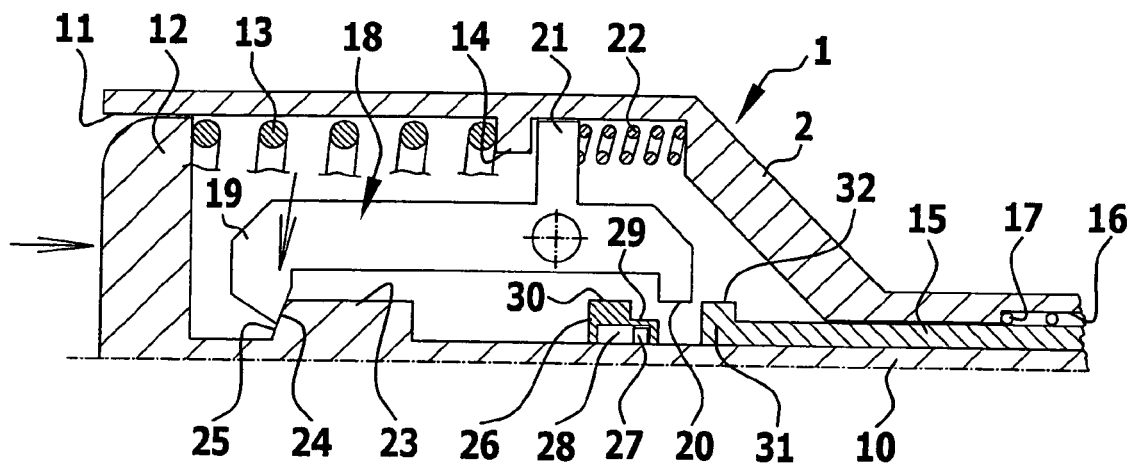
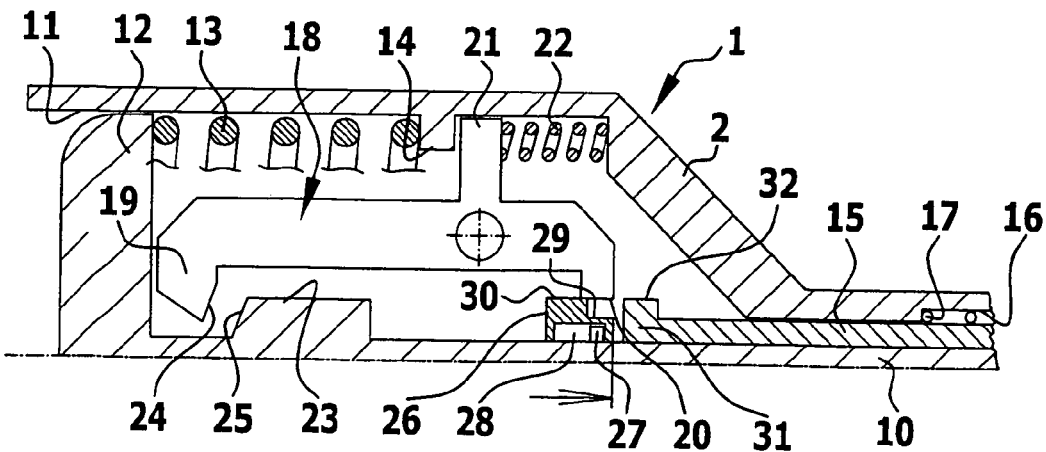

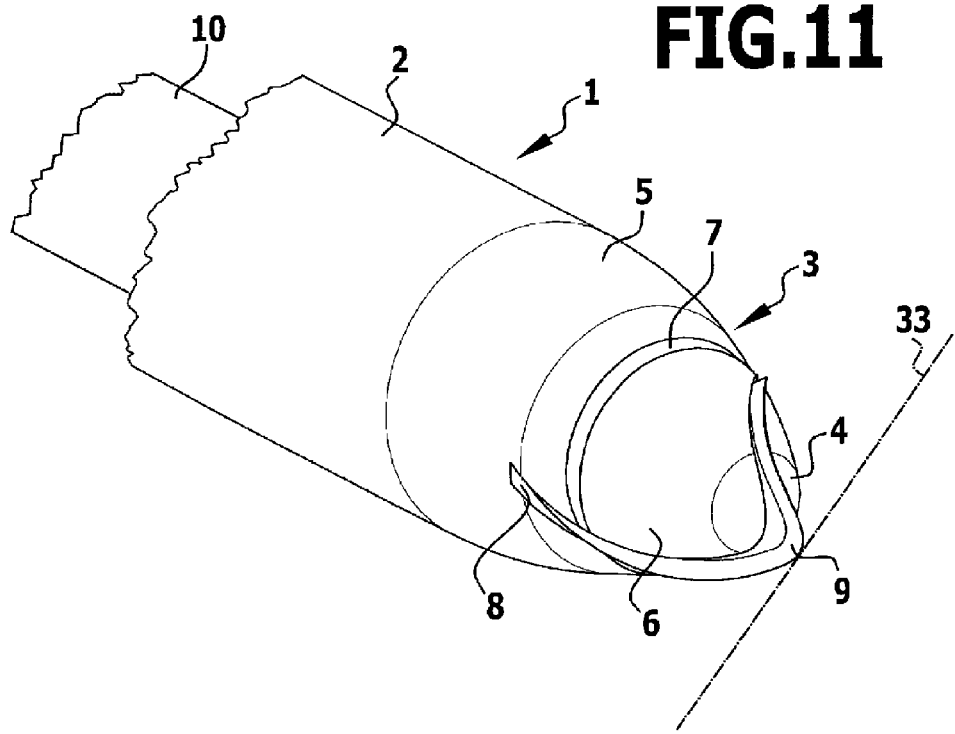
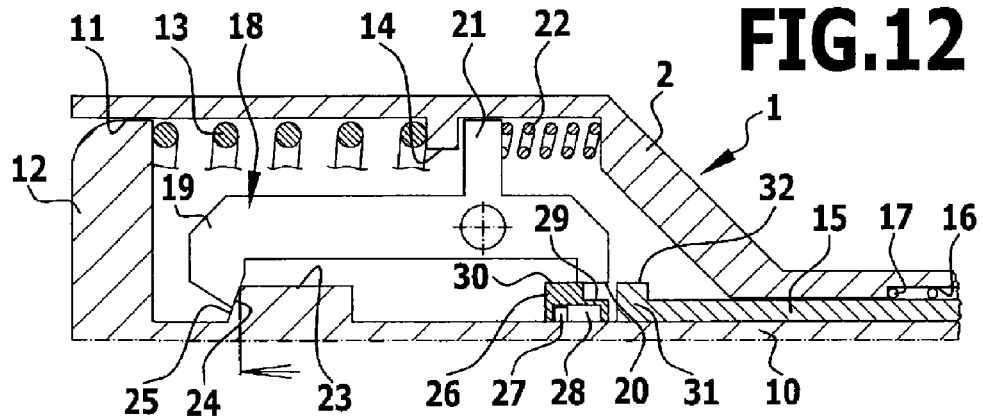

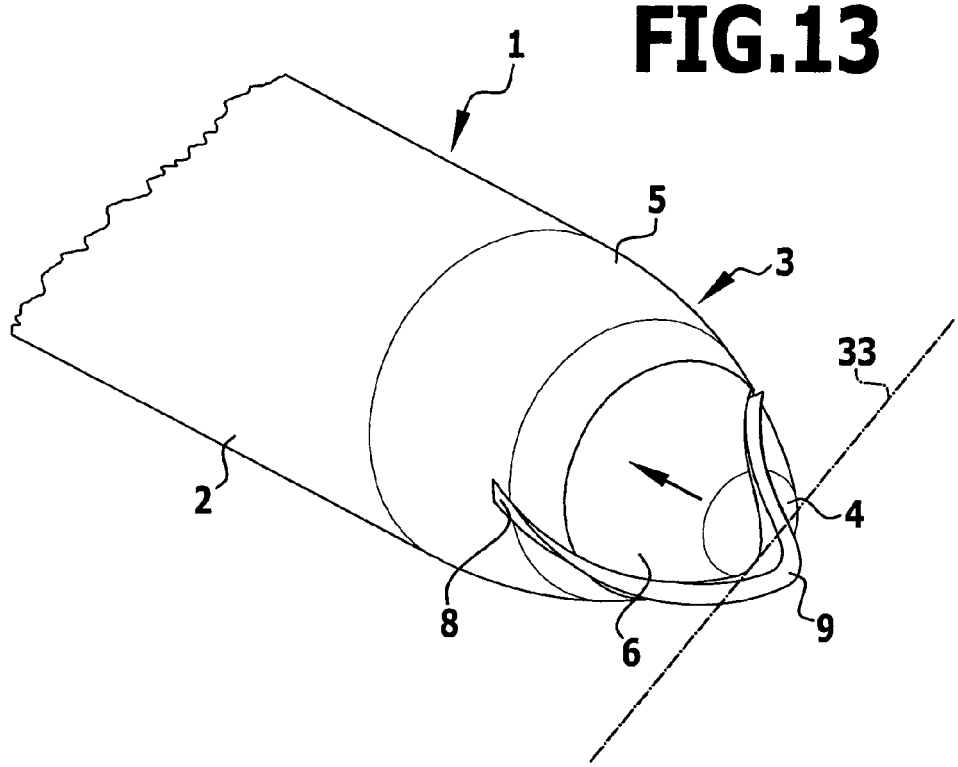
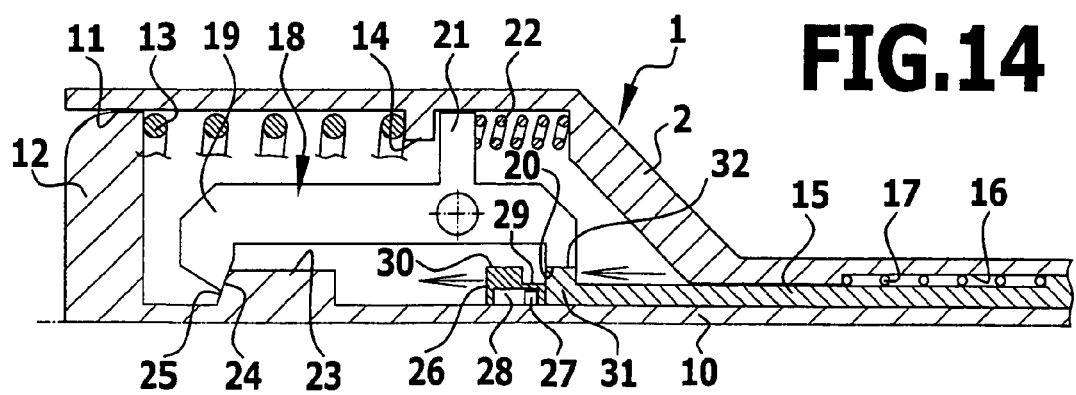

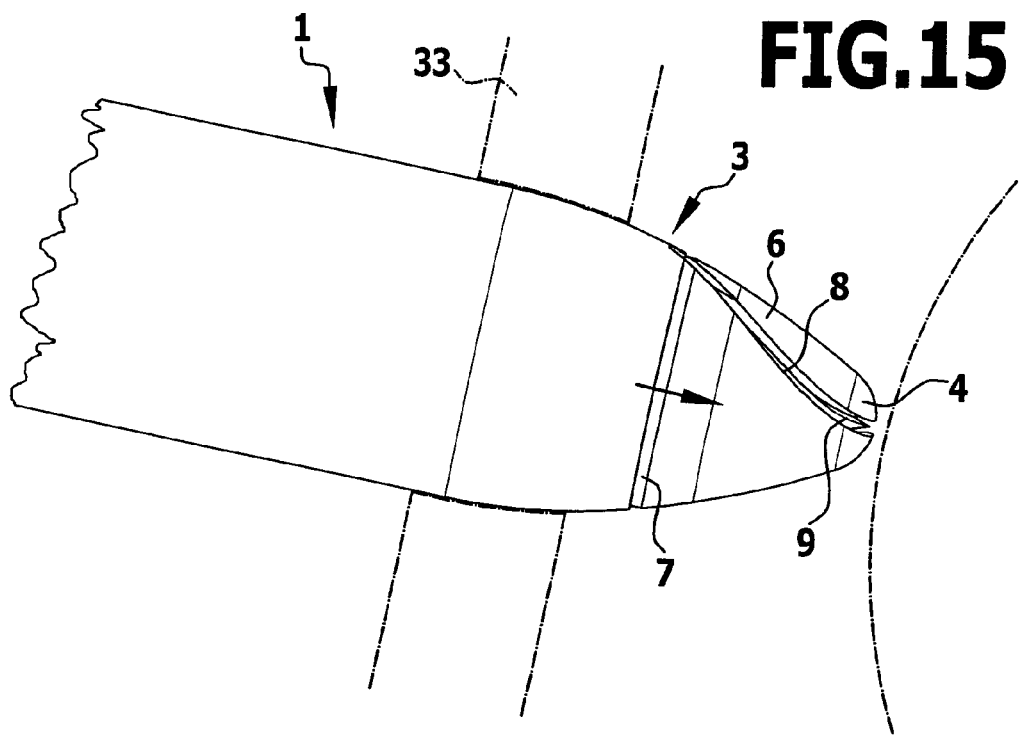
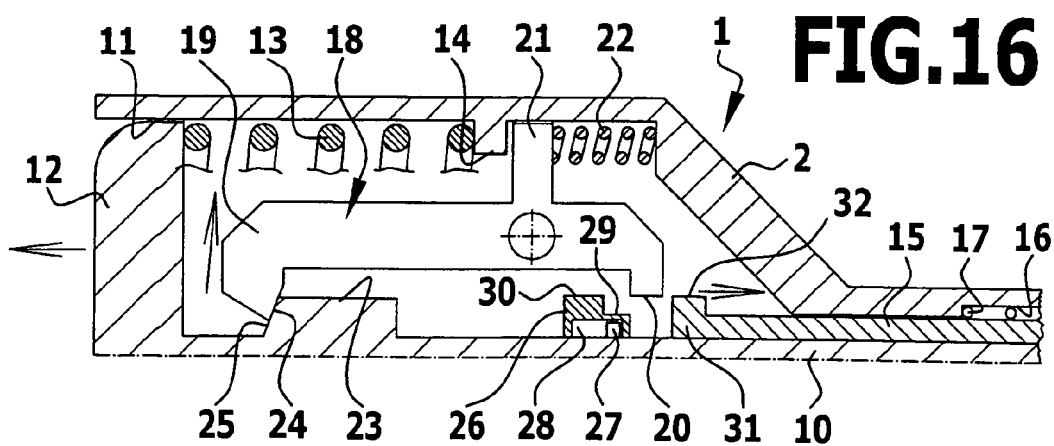

SURGICAL OBTURATOR

This application is a continuation of International patent application no. PCT/EP2007/003881 filed on May 3, 2007 and claims the benefit of German patent application no. 10 2006 024 757.4 filed May 27, 2006, each of which is incorporated herein and made a part hereof by reference.

BACKGROUND OF THE INVENTION

The invention relates to a surgical obturator for piercing a body wall, comprising a tubular housing that at one end forms an introduction tip with a continuously decreasing diameter, and comprising a blade projecting from the introduction tip for making an incision in the body wall.

Such obturators are used to form openings in a body wall for a cannula or a tube, which tube may be for example a trocar tube, through which instruments are introduced into the body.

When the obturator is being advanced, there is a risk that the obturator, once it has passed right through the body wall, may be advanced further in an uncontrolled manner and the blade disposed on the front end of the obturator may cause injury to internal organs.

It is therefore known to provide such obturators with a protective shield, which after passage through the body wall is pushed forward and covers the blade (WO89/03661). Advancing the protective shield can likewise lead to injuries, as it often shoots forward abruptly under the action of a spring, and it is moreover usually necessary for the obturator to have fully penetrated the body wall before activation of the protective shield may occur.

SUMMARY OF THE INVENTION

The object of the invention is to design a surgical obturator of the above general type in such a way that the risk of an injury to internal organs during piercing of a body wall is reduced.

In a surgical obturator of the type described in the introduction, this object is achieved according to the invention in that the introduction tip comprises a central protective cap, which is displaceable in longitudinal direction relative to the introduction tip between an advanced inoperative position and a retracted working position, that the blade in the housing is displaceable in longitudinal direction between an advanced cutting position and a retracted protected position, that disposed in the housing is a retraction device that displaces the blade from the cutting position into the protected position, and that the retraction device can be activated by a displacement of the protective cap from the working position into the inoperative position.

With such a development, the protection is effected by an active retraction of the blade into the housing. This retraction device is activated by the movement of a central protective cap, which in a working position is retracted and in an inoperative position is advanced. Such a protective cap is displaced into the working position by the positioning of the obturator against the body wall and moves during piercing of the body wall into the advanced inoperative position because the protective cap then no longer rests against the body wall and is therefore pushed back into the working position. This advancing movement of the protective cap is utilized in order immediately to retract the blade to such an extent that it no longer projects from the protective cap and the introduction tip, with the result that there is also no longer any risk of injury.

In this case, it is advantageous if the protective cap is acted upon by a spring that displaces the protective cap from the working position into the inoperative position. This occurs immediately after the piercing of the body wall, in which case the advancing movement of the protective cap may be very slight so that there is no danger of the protective cap causing an injury as a result of the advancing movement.

In particular it is provided that the blade in the protected position is retracted to such an extent that it also no longer projects from the protective cap in the working position thereof. Thus, even if the protective cap should come to lie against an internal organ and therefore be displaced once more into the working position, there is no risk of the blade coming into contact with internal organs. With the use of a protective shield that overlaps the blade, there is the risk that the protective shield may be accidentally pushed back and may then release the blade. In order to prevent that, special complicated locking devices have to be provided, which hold the protective shield in the advanced position. With the described design, this problem is eliminated because the blade remains in a retracted, protected position once the retraction device has been activated by the advancing of the protective cap.

In the cutting position the blade projects in the region of the retracted protective cap and in an adjoining region of the introduction tip from the contour of the protective cap and of the introduction tip.

In this case, it is advantageous if the blade in the cutting position does not project from the contour of the introduction tip in the proximal end region thereof. As a result of such a development, during piercing of the body wall an incision is made only in a central region of the introduction tip, not however in the region of the proximal edge. When the obturator is advanced further, the introduction tip, the diameter of which increases in proximal direction, enters the body wall through the opening produced by the incision and expands this opening without additional cutting in the end region. The result is therefore a relatively non-invasive production of an opening and moreover a good seal between the body wall and the obturator, so that it is optionally possible also to achieve a substantially gas-tight seal. This is important in the event of insufflation of the body cavity and when using sealed obturators.

In particular, the introduction tip may be of a truncated-cone-shaped configuration and have a rounded tip. In this case, the central part of the introduction tip is formed as a rule by the protective cap.

The use of a central protective cap to activate the retraction device moreover has the advantage that a retraction of the blade may already be initiated before the introduction tip has passed completely through the body wall. It is actually sufficient for the central protective cap, the outside diameter of which is smaller than the outside diameter of the introduction tip, to have passed through the body wall for a retraction of the blade to occur, despite the introduction tip not yet having been pushed completely through the body wall. By selecting the dimensions of the protective cap relative to the remaining introduction tip it is possible to define the instant, at which during piercing a retraction of the blade occurs. The smaller the diameter of the protective cap in relation to the diameter of the introduction tip, the earlier the activation of the retraction device occurs.

In a preferred embodiment, the blade is held on a blade carrier, which is mounted in a longitudinally displaceable manner in the housing and which is displaceable by means of a spring into a retracted position, in which the blade is situated in the protected position.

The blade carrier may carry a gripping element for displacing the blade carrier into the advanced position.

It is advantageous if the retraction device comprises a catch, which during advancing locks the blade carrier in the advanced position.

Given such a development, it may be provided that the protective cap during advancing from the working position into the inoperative position releases the catch and hence triggers the return movement of the blade carrier into the retracted position.

In a particularly preferred embodiment, the protective cap in the working position displaces a locking element into a position fixing the catch in a detent position and during advancing into the inoperative position removes the locking element from this position. As a result of the removal of the blocking element the catch is released and allows the blade carrier to move back into the protected position of the blade.

Of particular advantage is a development, in which the catch is held by a blocking member in a position fixing the catch in a detent position and in which the protective cap in the working position removes the blocking member from the catch and at the same time displaces the locking element into the position fixing the catch, in which case the catch remains constantly in its detent position.

Such a development allows a locking of the catch in the detent position even when the protective cap is not yet in working position, i.e. is still advanced in the inoperative position. As soon as the protective cap during piercing of the body wall is positioned against the outside of the body wall, it is therefore displaced into the working position and in this case replaces the blocking member with the locking element, i.e. the protective cap itself performs the function of locking the catch. Thus, the catch at the start of the operation is fixed in the detent position by means of the blocking member so long as the protective cap is still situated in the advanced inoperative position and the obturator has not yet been positioned against the body wall. At the start of the piercing operation, the protective cap as a result of being positioned against the body wall is retracted and effects the fixing of the catch in the detent position. This fixing lasts until the protective cap, after piercing, is advanced into the inoperative position and hence releases the catch. This leads to retracting of the blade.

The blocking member may be mounted on the blade carrier, wherein the mounting is in particular a displaceable mounting.

For example, the blocking member may be a sliding ring that surrounds the blade carrier and is freely displaceable between two end positions.

It is advantageous if the catch is a spring-loaded pivoted lever.

The catch and the blade carrier may have sliding faces, which, when the catch is not fixed in the detent position and the blade carrier is being pushed back, slide along one another and in so doing move the catch in a release position. The catch is therefore released in that the blade carrier is loaded with a force in the direction of the protected position of the blade, for example by means of a spring.

The shape of the blade may differ widely, being for example V-shaped, a blade having a helical-line-shaped cutting edge being particularly advantageous. Such a helical-line-shaped cutting edge facilitates the delicate insertion of the obturator into a body wall and also results in the blade during retraction being moved, by virtue of the guidance of the blade in a guide slot of the protective cap, helically and hence in accordance with the piercing motion that the surgeon carries out likewise in a helical-line-shaped manner.

BRIEF DESCRIPTION OF THE DRAWINGS

The following description of preferred embodiments of the invention is used in connection with the drawings to provide a detailed explanation. The drawings show:

FIG. 8: a partial longitudinal section through a housing of an obturator with a retraction device for the blade in a state corresponding to the retracted protected position of the blade;

FIG. 9: a view similar to FIG. 8 during the advancing of the blade from the protected position into the cutting position;

FIG. 10: a view similar to FIG. 9 with the blade fully advanced;

FIG. 11: a view similar to FIG. 1 with an obturator prior to positioning against a body wall and prior to displacement of the protective cap into the working position;

FIG. 12: a view similar to FIG. 10 with the blade carrier advanced and locked in the cutting position;

FIG. 13: a view similar to FIG. 11 with the obturator during piercing of a body wall with the protective cap in working position;

FIG. 14: a view similar to FIG. 12 with a pushed-back blade carrier;

FIG. 15: a diagrammatic side view of the obturator of FIG. 1 after piercing of the body wall and after retraction of the blade and FIG. 16: a view similar to FIG. 14 during the return movement of the blade carrier into the protected position of the blade.

DETAILED DESCRIPTION

Figure 1:
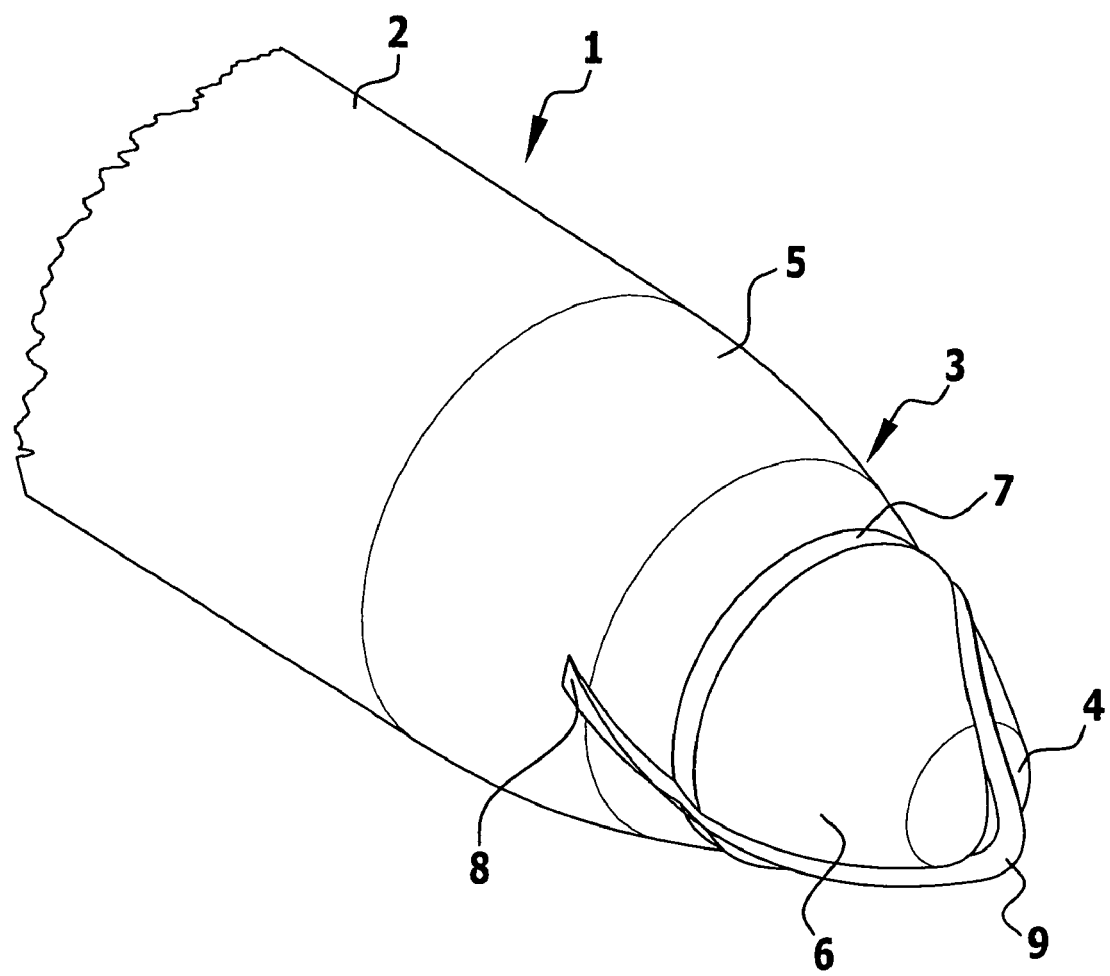
FIG. 1: a perspective view of an obturator in the region of the introduction tip.

The obturator 1 represented in the drawings comprises a tubular housing 2, of which in FIGS. 1, 11, 13 and 15 in each case only the front part is shown. The housing 2 terminates in this front part with a truncated-cone-shaped introduction tip 3, the tip 4 of which is rounded. The introduction tip 3 is subdivided into two portions, namely a proximal portion 5, which is part of the housing 2, and a central protective cap 6, which is displaceable relative to the housing and hence relative to the proximal portion 5 in axial direction between two end positions, namely a retracted (proximal) working position and an advanced (distal) inoperative position. In the retracted working position the outer surface of the protective cap 6 merges continuously into the outer surface of the proximal portion 5 (FIG. 13), in the advanced inoperative position a step 7 is formed between the protective cap 6 and the proximal portion 5 of the introduction tip 3 (FIG. 1).

Running through its tip 4 the protective cap 6 has a slot 8, which extends as far as into the proximal portion 5 of the introduction tip 3 but terminates in the region of this proximal region 5, i.e. does not extend as far as the proximal end of the proximal portion 5.

Projecting through this slot 8 is a blade 9, the cutting edge of which in the illustrated embodiment is of a helical-line-shaped configuration, this shape corresponding also to the shape of the slot 8. In this case, the cutting edge of the blade 9 in an advanced cutting position of the blade 9 extends with slight clearance relative to the protective cap 6 and the proximal portion 5 outside of these parts, and the blade 9 may be displaced into a retracted protected position, in which the blade 9 no longer projects from the slot 8, and indeed does not project even when the protective cap 6 has been displaced into the retracted working position.

Figure 2:
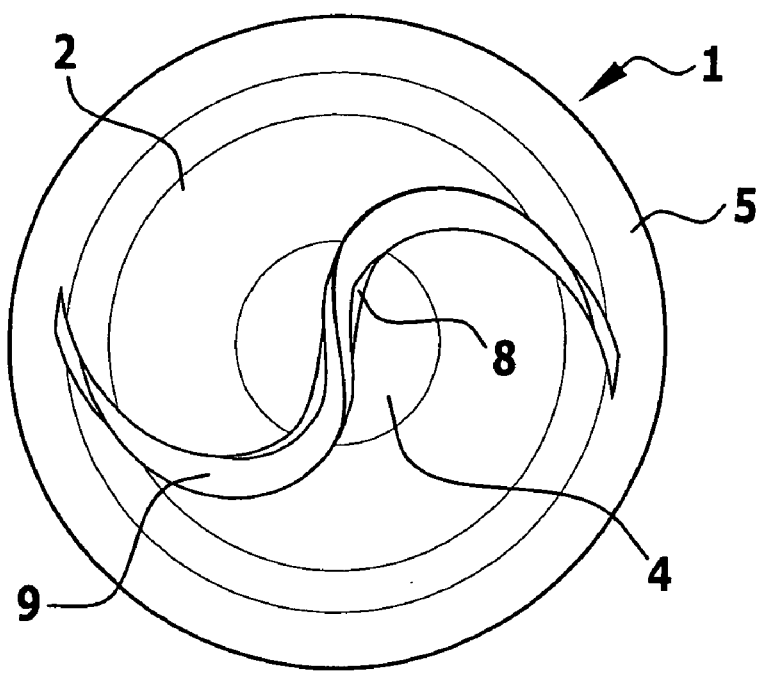
FIG. 2: a plan view of the obturator of FIG. 1.
Figure 3:
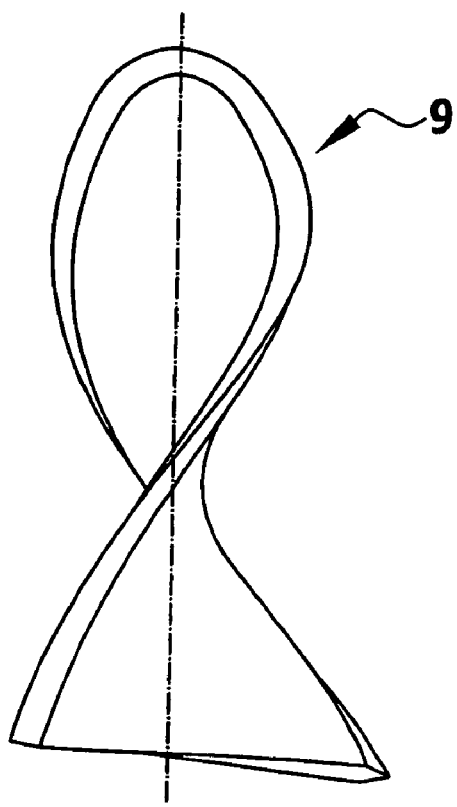
FIG. 3: a detail view of a blade with a helical-line-shaped cutting edge.
Figure 4:
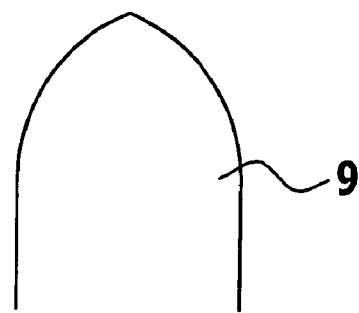
FIGS. 4 to 7: various embodiments of preferred contours of cutting edges.
Figure 5:
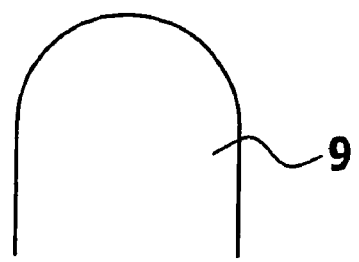
Figure 6:
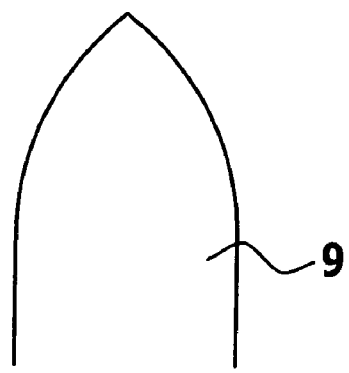
Figure 7:
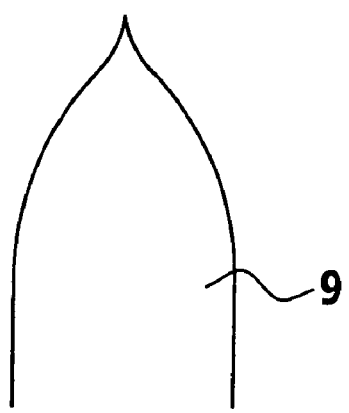

The contour of the blade 9 may differ widely, with it being possible to use in addition to the helical-line-shaped configuration according to FIGS. 1 to 3 V-shaped contours or similar contours, the important point being merely that the cutting edge projects in longitudinal direction of the obturator 1 from the introduction tip 3 and that the cutting edge extends over the tip 4 so that, when the obturator is advanced towards a body wall, starting from the tip a drawing incision is introduced into the body wall. FIGS. 4 to 7 illustrate possible contours of the blades 9, for example with a shallow or steep ogive (FIGS. 4 and 6), with a semi-circular contour (FIG. 5) or with an explicit formation of a tip (FIG. 7).

The blade 9 is held in the interior of the housing 2 on a blade carrier 10 that might optionally also be formed integrally with the blade 9, this blade carrier 10 extending through the entire housing 2 and closing an opening 11 at the opposite end of the housing 2 to the introduction tip 3 in the form of a pressure plate 12. Disposed in the interior of the housing 2 and lying adjacent to the inner wall thereof is a helical spring 13, which concentrically surrounds the blade carrier 10 and is supported on the one hand against the pressure plate 12 and on the other hand against an annular shoulder 14 of the housing 2 and which displaces the pressure plate 12 and hence the blade carrier 10 as well as the blade 9 into a retracted position that corresponds to the protected position of the blade. By means of a pressure upon the pressure plate 12 the unit of blade carrier 10 and blade 9 may be displaced counter to the action of the helical spring 13 in the direction of the introduction tip 3 so that the blade 9 moves into the cutting position, in which the cutting edge projects out through the slot 8.

The protective cap 6 is connected to a sleeve 15, which surrounds the blade carrier 10 and is used also to guide the protective cap 6 and by means of which the protective cap 6 is mounted in a longitudinally displaceable manner in the obturator 1. Disposed in an annular gap 16 between the inner wall of the housing 2 and the sleeve 15 is a helical spring 17, which is supported on the one hand against the inner wall of the housing 2 and on the other hand against the sleeve 15 and displaces the sleeve 15 and hence the protective cap 6 into the extended position corresponding to the inoperative position of the protective cap 6. The protective cap 6 may be pushed counter to the action of the helical spring 17 into the housing 2 and in this case moves into the working position.

A detent lever 18 is moreover mounted in the housing 2 so as to be pivotable about a pivotal axis extending transversely of the longitudinal axis and has on one end a detent projection 19 and on the opposite end a blocking face 20. By means of a helical spring 22, which is supported on the one hand against the inner wall of the housing 2 and on the other hand against a lateral projection 21, the detent lever 18 is pivoted into an initial position, in which the detent lever 18 extends parallel to the longitudinal direction. In this case, the projection 21 lies adjacent to the annular shoulder 14 (FIG. 9).

The blade carrier 10 has a lateral detent projection 23, which projects radially to such an extent that the detent projection 19 of the detent lever 18 engages into the path of motion of the detent projection 23 when the blade carrier 10 is displaced. Both the detent projection 19 and the detent projection 23 have oblique sliding faces 24, 25, which lie adjacent to one another when the blade carrier 10 is retracted from the advanced position into the retracted position.

The blade carrier 10 is surrounded by a sliding ring 26, which is mounted so as to be longitudinally displaceable along the blade carrier 10 and the longitudinal displacement of which along the blade carrier 10 is limited by means of a pin 27, which projects radially from the blade carrier 10 and engages into an internal groove 28 of the sliding ring 26 that extends transversely of the plane of the sliding ring 26. In a manner not evident from the drawing, the sliding ring 26 lies adjacent to the inner wall of the housing 2 and is displaceable relative to this inner wall. For the displacement, however, a specific force is needed in order to overcome the friction between sliding ring and inner wall. Consequently, upon a displacement of the blade carrier 10 and hence of the pin 27 the sliding ring is driven by the movement of the blade carrier only when the pin 27 strikes against the end of the internal groove 28.

The sliding ring 26 on its end facing the introduction tip 3 has a step-shaped recess 29, the outer surface 30 situated alongside said recess being disposed in the same plane as an outer surface 32 of an annular flange 31 that is formed on the end of the sleeve 15 by this annular flange.

When the obturator 1 is used, the blade carrier 10 is initially in the retracted position, in which it is displaced by means of the helical spring 13, the blade 9 therefore being situated in the retracted protected position. In the retracted position of the blade carrier 10 the detent projection 19 of the detent lever 18 is supported on the detent projection 23, with the result that the detent lever 18 is pivoted out of the initial position counter to the action of the helical spring 22 (FIG. 8). The blocking face 20 of the detent lever 18 in this case engages into a gap between the sliding ring 26 and the annular flange 31. The protective cap 6 and the sleeve 15 are displaced by the helical spring 17 into the advanced position, i.e. the protective cap 6 is situated in its inoperative position. In this position of the protective cap 6 and the blade 9, the protective cap 6 covers the blade and the blade does not project from the slot 8. The protective cap 6 cannot be displaced into the retracted working position, this being prevented by the engagement of the detent lever 18 between the sliding ring 26 and the annular flange 31.

In order to insert the obturator 1, it has to be activated. This is effected by a pressure upon the pressure plate 12 so that the pressure plate 12 is displaced counter to the action of the helical spring 13. In this case, first the detent projection 19 slides down off the detent projection 23, thereby allowing the detent lever 18 to pivot under the action of the helical spring 22 back into the initial position (FIG. 9).

As the pressure plate 12 is advanced further, the sliding ring 26 moves with its outer surface 30 under the blocking face 20 of the detent lever 18 (FIG. 10).

If the user then releases the pressure plate, the blade carrier 10 under the action of the helical spring 13 shifts back a little into the retracted position but at the same time the detent projection 23 moves into abutment with the detent projection 19, which prevents any further return movement of the blade carrier 10. The detent lever 18 moreover rests on the outer surface 30 of the sliding ring 26, which as a result of the clamping action between sliding ring 26 and blocking face 20 during this return movement of the blade carrier 10 is displaced relative to the blade carrier 10, with it remaining constant in terms of its position relative to the blocking face 20. As a result of this abutment of the outer surface 30 of the sliding ring 26 with the blocking face 20 of the detent lever 18, the detent lever 18 is prevented from pivoting out of the initial position and therefore blocks the full return movement of the blade carrier 10 into the retracted position (FIG. 12). By means of the oblique sliding faces 24 and 25 and under the action of the helical spring 13, which endeavours to displace the blade carrier 10 into the retracted position, the detent lever 18 experiences a torque that presses its blocking face 20 forcefully against the outer surface 30 of the sliding ring 26, thereby ensuring that this blocking is maintained (FIG. 12).

In this position the blade 9 is advanced into the cutting position but is still encased by the protective cap 6, which in turn is situated under the action of the helical spring 17 in the advanced inoperative position (FIGS. 11 and 12).

When the obturator 1 is advanced towards a body wall 33, the tip of the protective cap 6 is positioned against the body wall 33 and therefore pushed back counter to the action of the spring 17 so that the blade 9, which is in the cutting position, is released and, when the obturator 1 is advanced further, pierces the body wall with an incision. The protective cap 6 in this case remains in position against the body wall 33 and is therefore pushed back permanently into the working position. A further result of this backward movement is that the sleeve 15 by means of its annular flange 31 pushes the sliding ring 26 back relative to the blade carrier 10, the annular flange 31 at the same time moving under the blocking face 20 of the detent lever 18 and therefore effecting the fixing of the detent lever 18 in the axial initial position. The detent lever 18 therefore remains locked in the detent position, the locking in this case being effected at the start of the backward movement of the sleeve 15 by means of the sliding ring 26 and at the end by means of the annular flange 31 (FIG. 14).

As soon as the obturator 1 has been advanced through the body wall 33 to such an extent that the protective cap 6 is disposed inside the body wall 33 (FIG. 15), the protective cap 6 may be displaced under the action of the helical spring 17 forward into the inoperative position since it is no longer pushed back by the body wall 33. A further result of this advancing of the protective cap 6 into the inoperative position is that the annular flange 31 under the blocking face 20 is pulled away, i.e. the locking of the detent lever 18 is discontinued and the detent lever 18 may be pivoted out of the paraxial initial position counter to the action of the spring 22.

Such a pivoting is effected by virtue of the backward sliding movement of the blade carrier 10 under the action of the helical spring 13. During this return movement the sliding faces 24, 25 of the two detent projections 19 and 23 slide along one another, thereby allowing the detent projection 23 to slide past the pivoted detent lever 18 and the detent projection 19 thereof into the retracted position, in which the blade is in the protected position (FIG. 16). The advancing of the protective cap 6 into the inoperative position therefore triggers a backward sliding movement of the blade 9 into the protected position, with the result that the blade 9 no longer projects from the slot 8 and so the risk of injury ceases to exist as soon as the protective cap 6 has passed through the body wall 33.

This instant is reached before the introduction tip 3 has fully penetrated the body wall 33 because the outside diameter of the protective cap 6 is smaller than the outside diameter of the introduction tip 3. Once the introduction tip 3 has been completely pushed through into the interior of the body, the opening produced by the blade 9 is expanded without this entailing a further incision, because the blade 9 in this case is already in the protected position.

What is claimed is:

1. Surgical obturator for piercing a body wall, comprising:
    a tubular housing that at one end forms an introduction tip with a continuously decreasing diameter,
    a blade projecting from the introduction tip for making an incision in the body wall,
    a blade carrier which carries the blade, the blade carrier being mounted in a longitudinally displaceable manner in the housing,
    the introduction tip comprising two portions, a proximal portion, which is part of the housing, and a central protective cap, which is displaceable in a longitudinal direction relative to the housing between an advanced inoperative position and a retracted working position,
    a retraction device disposed in the housing which comprises:
        a first spring for displacing the blade carrier in the longitudinal direction from an advanced cutting position into a retracted protected position, and
        a catch, which during advancement of the blade carrier locks the blade carrier in the advanced cutting position,
    the retraction device being activated by a displacement of the protective cap from the working position into the inoperative position,
    wherein:
        the outer surface of the protective cap in the retracted working position merges continuously into the outer surface of the proximal portion,
        in the advanced inoperative position a step is formed between the protective cap and the proximal portion of the introduction tip,
        the blade in the cutting position projects in a region of the retracted protective cap and in a distal region of the proximal portion from a contour of the protective cap and a contour of the distal region of the proximal portion, and
        the protective cap during the displacement from the working position into the inoperative position releases the catch and triggers the displacement of the blade carrier into the retracted position.

2. Surgical obturator according to claim 1, wherein the blade in the protected position is retracted to such an extent that it no longer projects from the protective cap in the working position of the protective cap.

3. Surgical obturator according to claim 1, wherein the protective cap is acted upon by a second spring that displaces the protective cap from the working position into the inoperative position.

4. Surgical obturator according to claim 1, wherein the blade in the cutting position does not project from the contour of the proximal portion of the introduction tip in a proximal end region of the proximal portion.

5. Surgical obturator according to claim 1, wherein the introduction tip is of a truncated-cone-shaped configuration and has a rounded tip.

6. Surgical obturator according to claim 1, wherein the blade carrier carries a gripping element for displacing the blade carrier into the advanced cutting position.

7. Surgical obturator according to claim 1, wherein the protective cap in the working position displaces a locking element into a position fixing the catch in a detent position and during advancing into the inoperative position removes the locking element from the detent position.

8. Surgical obturator according to claim 7, wherein:
    the catch is held by means of a blocking member in a position fixing the catch in the detent position, and
    the protective cap in the working position removes the blocking member from the catch and at the same time displaces the locking element into the position fixing the catch, so that the catch remains continuously in its detent position.

9. Surgical obturator according to claim 8, wherein the blocking member is mounted on the blade carrier.

10. Surgical obturator according to claim 9, wherein the blocking member is mounted displaceably on the blade carrier.

11. Surgical obturator according to claim 10, wherein the blocking member is a sliding ring that surrounds the blade carrier and is freely displaceable between two end positions.

12. Surgical obturator according to claim 1, wherein the catch is a spring-loaded pivotal lever.

13. Surgical obturator according to claim 1, wherein the catch and the blade carrier have sliding faces, which, when the catch is not fixed in a detent position and the blade carrier is being pushed back, slide along one another and in so doing move the catch into a release position.

14. Surgical obturator according to claim 1, wherein the blade has a helical-line-shaped cutting edge.

15. Surgical obturator according to claim 4, wherein the blade has a helical-line-shaped cutting edge.

16. Surgical obturator according to claim 5, wherein the blade has a helical-line-shaped cutting edge.

17. Surgical obturator according to claim 1, wherein the blade is integrally formed with the blade carrier.

* * * * *